(12) United States Patent
Sekiguchi et al.

(10) Patent No.: US 12,303,107 B2
(45) Date of Patent: May 20, 2025

(54) INSERTION DEVICE HAVING OPERATION LEVER MORE EASILY BENDABLE IN PREDETERMINED DIRECTION AND OPERATION PORTION OF INSERTION DEVICE

(71) Applicant: OLYMPUS CORPORATION, Tokyo (JP)

(72) Inventors: Yuta Sekiguchi, Hachioji (JP); Natsuki Hori, Yokohama (JP); Hidetsugu Tanaka, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 479 days.

(21) Appl. No.: 17/730,711

(22) Filed: Apr. 27, 2022

(65) Prior Publication Data

US 2022/0257090 A1 Aug. 18, 2022

Related U.S. Application Data

(63) Continuation of application No. PCT/JP2019/043704, filed on Nov. 7, 2019.

(51) Int. Cl.
*A61B 1/005* (2006.01)
*A61B 1/00* (2006.01)

(52) U.S. Cl.
CPC ........ *A61B 1/0052* (2013.01); *A61B 1/00078* (2013.01); *A61B 1/00096* (2013.01); *A61B 1/00042* (2022.02)

(58) Field of Classification Search
None
See application file for complete search history.

(56) References Cited

U.S. PATENT DOCUMENTS 4,348,556 A * 9/1982 Gettig ................ G05G 9/04796
200/6 A
4,538,035 A * 8/1985 Pool ................... G05G 9/04785
200/557

(Continued)

FOREIGN PATENT DOCUMENTS

EP 3 202 302 A1 8/2017
JP S58-038568 Y2 9/1983

(Continued)

OTHER PUBLICATIONS

International Search Report dated Feb. 4, 2020 received in PCT/JP2019/043704.

*Primary Examiner* — John P Leubecker
(74) *Attorney, Agent, or Firm* — Scully, Scott, Murphy & Presser, P.C.

(57) ABSTRACT

An insertion device includes a bending portion provided in an insertion portion having a longitudinal axis; an operation lever provided in an operation portion and configured to cause the bending portion to bend, where the operation portion is provided on a proximal end side of the insertion portion; and an elastic member connected to the operation portion, and provided with rigidity that resists tilting when the operation lever is tilted, where first rigidity in a first tilting direction is lower than second rigidity in a second tilting direction, wherein the elastic member, a cross-section orthogonal to an axial direction of the operation lever is formed into a rectangular shape, and any of corners of the rectangular shape of the cross-section is placed in the first tilting direction.

20 Claims, 6 Drawing Sheets

(56) References Cited

U.S. PATENT DOCUMENTS

| | | | | |
|---|---|---|---|---|
| 5,373,317 | A * | 12/1994 | Salvati | G02B 23/2476 348/66 |
| 5,400,769 | A * | 3/1995 | Tanii | A61B 1/0016 600/152 |
| 5,473,325 | A * | 12/1995 | McAlindon | G06F 3/0219 341/20 |
| 5,804,781 | A * | 9/1998 | Okabe | G05G 9/047 200/6 A |
| 2002/0024503 | A1* | 2/2002 | Armstrong | G05G 9/047 345/167 |
| 2005/0121297 | A1* | 6/2005 | Sunadome | G05G 9/047 200/6 A |
| 2008/0264728 | A1* | 10/2008 | Kamiya | G05G 9/047 187/222 |
| 2013/0338441 | A1* | 12/2013 | Okamoto | A61B 1/0052 600/146 |
| 2017/0196435 | A1* | 7/2017 | Sato | G02B 23/24 |
| 2019/0223691 | A1* | 7/2019 | Takatsuji | A61B 1/0057 |
| 2020/0229681 | A1* | 7/2020 | Wang | A61B 1/0057 |

FOREIGN PATENT DOCUMENTS

| | | |
|---|---|---|
| JP | 2005-174651 A | 6/2005 |
| JP | 2007-172337 A | 7/2007 |
| JP | 2011-028342 A | 2/2011 |
| JP | 2013-039188 A | 2/2013 |
| WO | 2016/052147 A1 | 4/2016 |

* cited by examiner

INSERTION DEVICE HAVING OPERATION LEVER MORE EASILY BENDABLE IN PREDETERMINED DIRECTION AND OPERATION PORTION OF INSERTION DEVICE

CROSS REFERENCE TO RELATED APPLICATION

This application is a continuation application of PCT/JP2019/043704 filed on Nov. 7, 2019, the entire contents of which are incorporated herein by this reference.

BACKGROUND OF THE INVENTION

1. Field of the Invention

The present invention relates to an insertion device, such as a flexible endoscope, a rigid endoscope, a treatment instrument, and a medical manipulator, provided with a joystick used to bend a bending portion of an insertion portion in a desired direction.

2. Description of the Related Art

As is well known, endoscopes, which are insertion devices, are widely used for observation, treatment, and the like in a living body (in body cavities) or for inspection, repair, and the like in industrial plant equipment. An endoscope includes an insertion portion to be inserted into a bending tract or conduit.

Among such endoscopes, as disclosed, for example, in Japanese Patent Application Laid-Open Publication No. 2013-39188, endoscopes equipped with a joystick-type bending operation lever for use to bend a bending portion provided in an insertion portion are well known.

SUMMARY OF THE INVENTION

An insertion device according to one aspect of the present invention includes: an insertion portion having a longitudinal axis; a bending portion provided in the insertion portion and configured to be bendable from the longitudinal axis in all directions including up, down, left, and right directions; an operation portion provided on a proximal end side of the insertion portion; an operation lever provided in the operation portion and provided with a shaft body configured to cause the bending portion to bend in any of the all directions when the operation lever is tilted in a predetermined direction by a user; and an elastic member provided covering the shaft body, connected to the operation portion, and provided with rigidity that resists tilting when the operation lever is tilted, first rigidity in a first tilting direction being lower than second rigidity in a second tilting direction, wherein of the elastic member, a cross-section orthogonal to an axial direction of the operation lever is formed into a rectangular shape, and any of corners of the rectangular shape of the cross-section is placed in the first tilting direction.

An operation portion of an insertion device according to another aspect of the present invention includes: an operation lever provided with a shaft body configured to cause a bending portion of an insertion portion having a longitudinal axis to bend from the longitudinal axis in all directions including up, down, left, and right directions when the operation lever is tilted in a predetermined direction; and an elastic member provided covering the shaft body, connected to the operation portion, and provided with rigidity that resists tilting when the operation lever is tilted, first rigidity in a first tilting direction being lower than second rigidity in a second tilting direction, wherein of the elastic member, a cross-section orthogonal to an axial direction of the operation lever is formed into a rectangular shape, and any of corners of the rectangular shape of the cross-section is placed in the first tilting direction.

DETAILED DESCRIPTION OF THE PREFERRED EMBODIMENT

An aspect of an endoscope serving as an insertion device according to the present invention will be described below. In the following description, it should be noted that the drawings in each embodiment are schematic, that relationships between thickness and width of each component as well as ratios of the thickness among individual components are different from actual ones, and that dimensional relationships or ratios may not be uniform among the drawings.

Although the endoscope in the following description of a configuration is a so-called endoscope for examination of the ear, nose and throat having a small-diameter insertion portion, this is not restrictive, and the technique is also applicable to a so-called flexible endoscope provided with a flexible insertion portion for insertion into a bronchus or upper or lower digestive tract in a living body and to a so-called rigid endoscope provided with a rigid insertion portion and intended for surgical use.

An endoscope, which is an insertion device according to one aspect of the present invention, will be described below based on the drawings.

Figure 1:
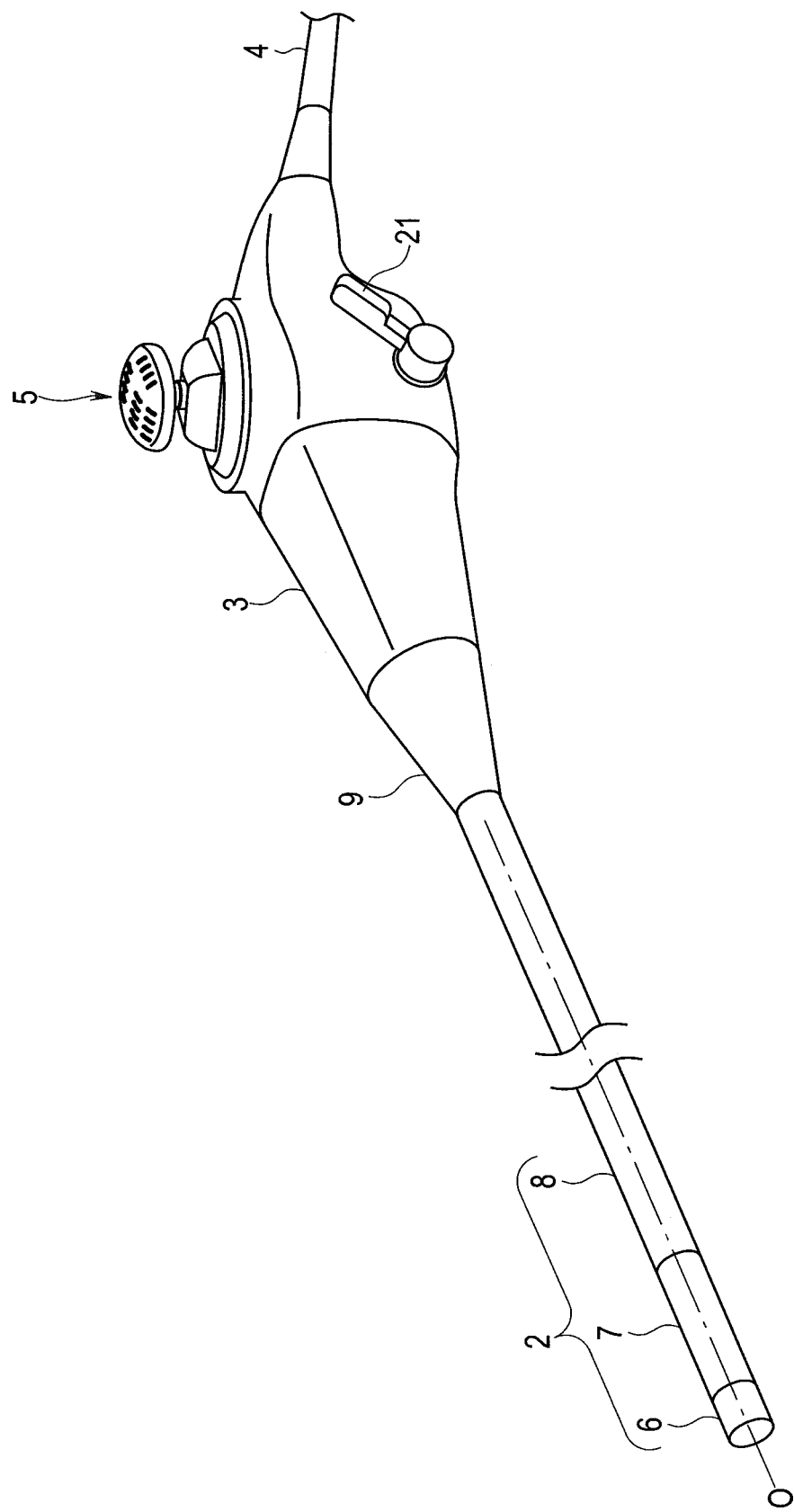
FIG. 1 is a diagram showing an external appearance of an endoscope, which is an insertion device according to one aspect of the present invention.

As shown in FIG. 1, the insertion device according to the present embodiment is an endoscope 1 serving as an electronic endoscope. The endoscope 1 includes a long, small-diameter insertion portion 2 having an outside diameter of approximately 3 to 4 mm, provided with a longitudinal axis O, and configured to be inserted into a subject, an operation portion 3 installed consecutively on a proximal end side of the insertion portion 2, and a universal cord 4, which is an endoscopic cable extended from the operation portion 3.

Note that a non-illustrated endoscope connector is provided on a terminal of the universal cord 4. The endoscope connector is connected to a video processor and a light source device of a non-illustrated external apparatus.

The insertion portion 2 is a tubular member having flexibility, and includes a distal end portion 6, a bending portion 7, and a flexible tubular portion 8 formed consecutively in this order from a distal end side. Image pickup means, illumination means, and the like are housed and placed in the distal end portion 6 of the components mentioned above.

The bending portion 7 is configured to be able to bend actively in four directions including left and right directions as well as up and down directions (all directions around an axis, including directions set by UP, DOWN, LEFT, and RIGHT operations: UP-DOWN/LEFT-RIGHT) with respect to the longitudinal axis O of the insertion portion 2.

The flexible tubular portion 8 is a tubular member formed to have passive flexibility, An image pickup cable, an after-mentioned light guide bundle, and the like (none is shown here) are passed through the flexible tubular portion 8, where the image pickup cable is extended from an image pickup apparatus (not shown) incorporated in the distal end portion 6, further extending through the operation portion 3 into the universal cord 4 and the light guide bundle is used to guide illuminating light from the light source device and emit the illuminating light from the distal end portion 6.

The operation portion 3 is provided, on the distal end side, with a bend preventing portion 9 connected to the flexible tubular portion 8 by covering a proximal end of the flexible tubular portion 8 of the insertion portion 2.

The operation portion 3 includes, as joystick-type endoscope operation means, a joystick lever mechanism 5, which is a bending operation portion making up a bending operation lever used to bend the bending portion 7 and a bending lock lever 21 used to lock a bent state of the bending portion 7 bent by the joystick lever mechanism 5.

Note that the operation portion 3 is provided with non-illustrated various multiple swatches and the like used to perform respective operations of the image pickup means, the illumination means, and the like.

The universal cord 4 is a complex cable through which a light guide bundle and the like are passed to transmit illuminating light from a signal cord bundle and the light source device (not shown) by passing from the distal end portion 6 of the insertion portion 2 through the insertion portion 2 to the operation portion 3.

Here, a configuration of the joystick lever mechanism 5 provided on the operation portion 3 of the endoscope 1 according to the present embodiment will be described in detail below.

Figure 2:
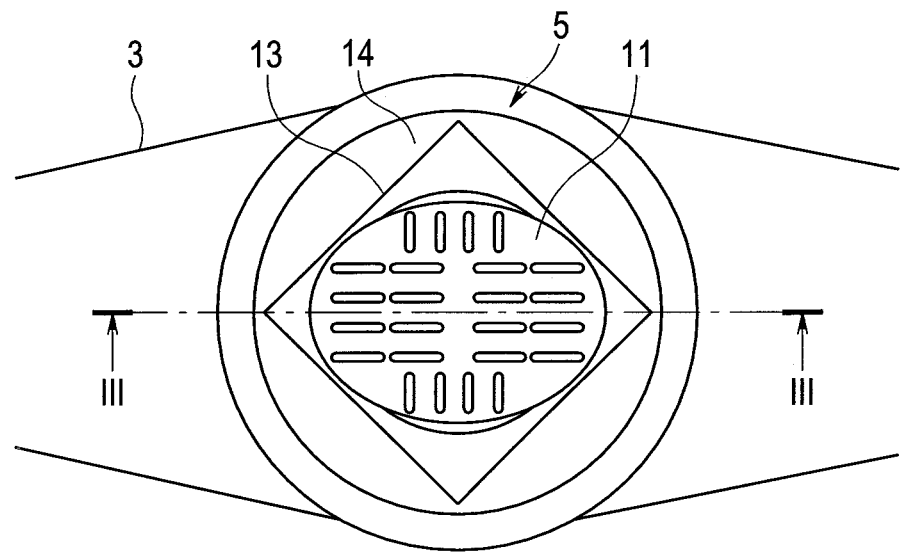
FIG. 2 is a plan view showing a configuration of a joystick lever mechanism provided on an operation portion of the endoscope.
Figure 3:
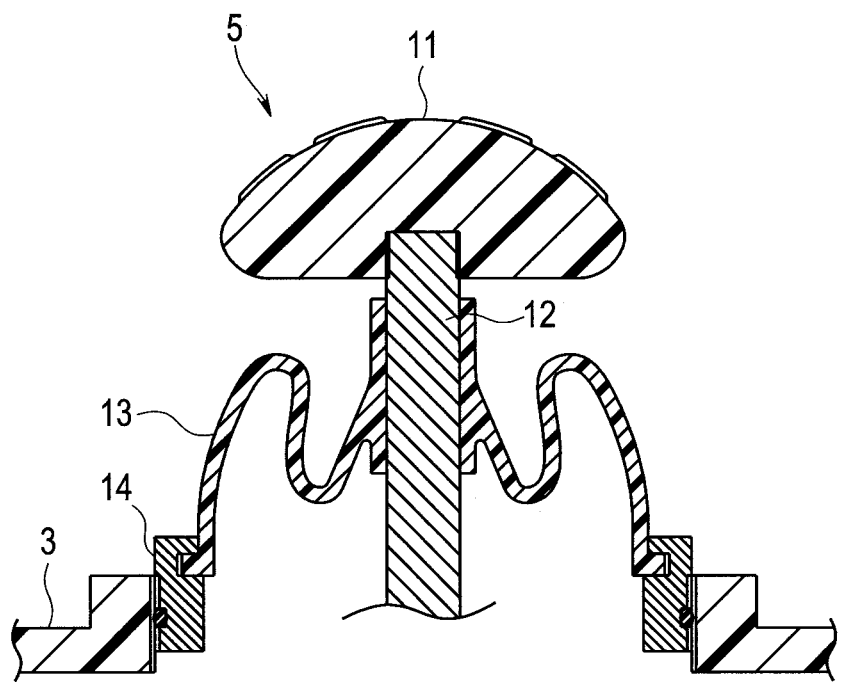
FIG. 3 is a cross-sectional view taken along line 111411 in FIG. 2, showing the configuration of the joystick lever mechanism of the endoscope.

As shown in FIGS. 2 and 3, the joystick lever mechanism 5 according to the present embodiment is placed protruding above a housing of the operation portion 3.

The joystick lever mechanism 5 includes a finger rest portion 11 for use by an operator to put a finger, a rod 12, and a rubber boot 13, which is a cover member formed by covering an entire circumference of the rod 12 and formed of an elastic member. Multiple non-slip projecting portions are provided on a surface of the finger rest portion 11.

Note that a specific configuration in which the bending portion 7 is driven in a bendable manner by tilting of the joystick lever mechanism 5 is well known, and thus description of the configuration and operation will be omitted.

As shown in FIG. 3, the rubber boot 13, which is an elastic member, includes a cylindrical member closely fixed to the rod 12 in a central part and a cross-section of the rubber boot 13 has a wavy meandering shape. Note that an entire circumference of an outside edge of the rubber boot 13 is fixed in a watertight manner to the housing of the operation portion 3 by a stopper ring 14.

Figure 4:
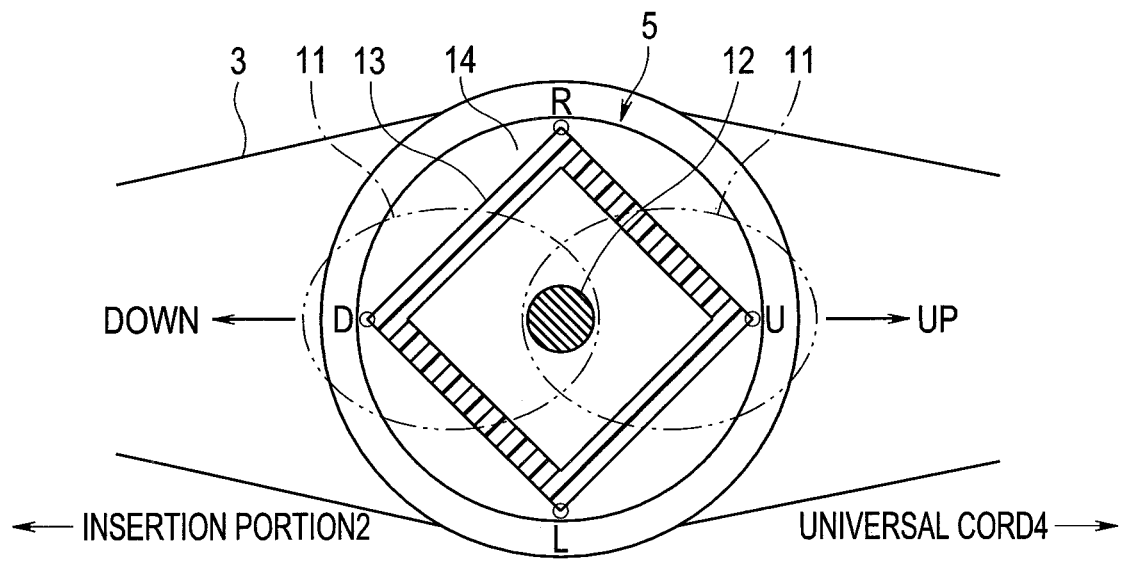
FIG. 4 is a partial cross-sectional view showing the joystick lever mechanism set to bend a bending portion in up and down directions of the endoscope.
Figure 5:
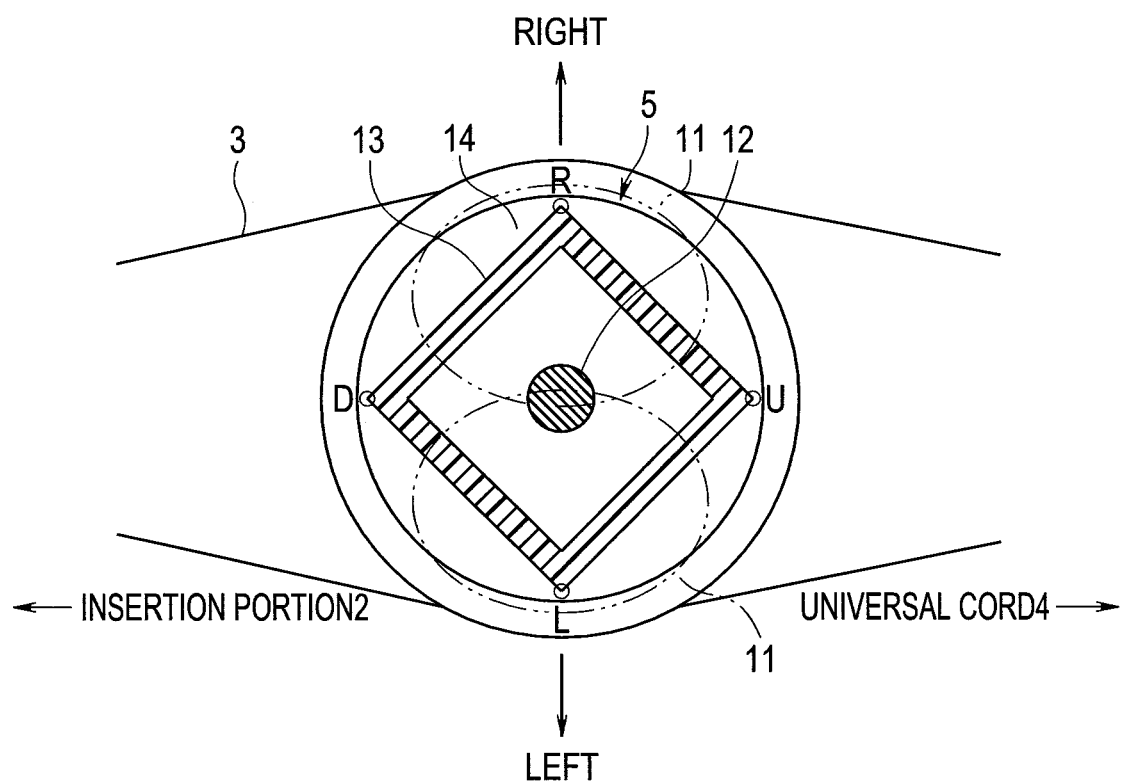
FIG. 5 is a partial cross-sectional view showing the joystick lever mechanism set to bend the bending portion in left and right directions of the endoscope.

As shown in FIGS. 4 and 5, an outer circumferential shape of the rubber boot 13 in a cross-sectional direction orthogonal to the rod 12 is a rectangular shape, which is a rhombic shape here with vertices U, D, R, and L at four corners being placed in front, back, left, and right directions of the operation portion 3.

Directions in which the rod 12 is tilted when the finger rest portion 11 is thumb-operated or otherwise operated by the user have been defined to allow the bending portion 7 to be bent in response to operations in the front, back, left, and right directions.

Specifically, as shown in FIG. 4, when the rod 12 is inclined rearward to the near side, i.e., toward the vertex U at a corner of the rubber boot 13 by thumb-operating the finger rest portion 11 toward the universal cord 4, the bending portion 7 bends upward (UP). On the other hand, when the rod 12 is inclined forward, i.e., toward the vertex D at a corner of the rubber boot 13 by thumb-operating the finger rest portion 11 toward the insertion portion 2, the bending portion 7 bends downward (DOWN).

As shown in FIG. 5, when the rod 12 is inclined leftward or rightward, i.e., toward the vertex L or R at a corner of the rubber boot 13 by thumb-operating the finger rest portion 11 to the left or right orthogonally to the front-rear direction of the operation portion 3, the bending portion 7 bends to the left (LEFT) or right (RIGHT).

Furthermore, when the rod 12 is tilted in a combination of all directions, including directions set by up, down, left, and right (UP, DOWN, LEFT, and RIGHT) operations, around the axis of the rod 12, the bending portion 7 can be bent in all directions.

During such bending operation of the bending portion 7, by tilting the rod 12 by aiming at the vertices U, D, R, and L at the four corners of the rubber boot 13 through thumb-operation or the like on the finger rest portion 11, the user can bend the bending portion 7 accurately in the frequently-used up, down, left, and right (UP, DOWN, LEFT, and RIGHT) directions without deviation.

As described above, the endoscope 1 according to the present embodiment is configured as follows: the outer circumferential shape of the rubber boot 13 of the joystick lever mechanism 5 is set to be rectangular, and the rubber boot 13 is placed in the operation portion 3 such that the outer circumferential shape is rhombic with the corners of the rubber boot 13 being aligned, respectively, with the directions in which the rod 12 is tilted when the finger rest portion 11 is thumb-operated or otherwise operated to bend the bending portion 7 in the up, down, left, and right directions.

This makes it easy for the user, to set directions of tilting operation to aiming directions (four—up, down, left, and right—directions) corresponding to the corners of the rubber boat 13 when thumb-operating or otherwise operating the finger rest portion 11 of the joystick lever mechanism 5 during bending operation of the bending portion 7. Consequently, when bending the bending portion 7 in any of frequently—used four—up, down, left, and right—directions, the user can operate the joystick lever mechanism 5 rectilinearly toward the appropriate corner of the rubber boot 13, and thus can avoid tilting the rod 12 obliquely in an unintended direction.

Thus, the endoscope 1, which is an insertion device according to the present embodiment, can be configured to make it easy to recognize the directions in which the bending portion 7 is to be bent using the joystick lever mechanism 5, which is a bending operation lever.

First Modification

Figure 6:
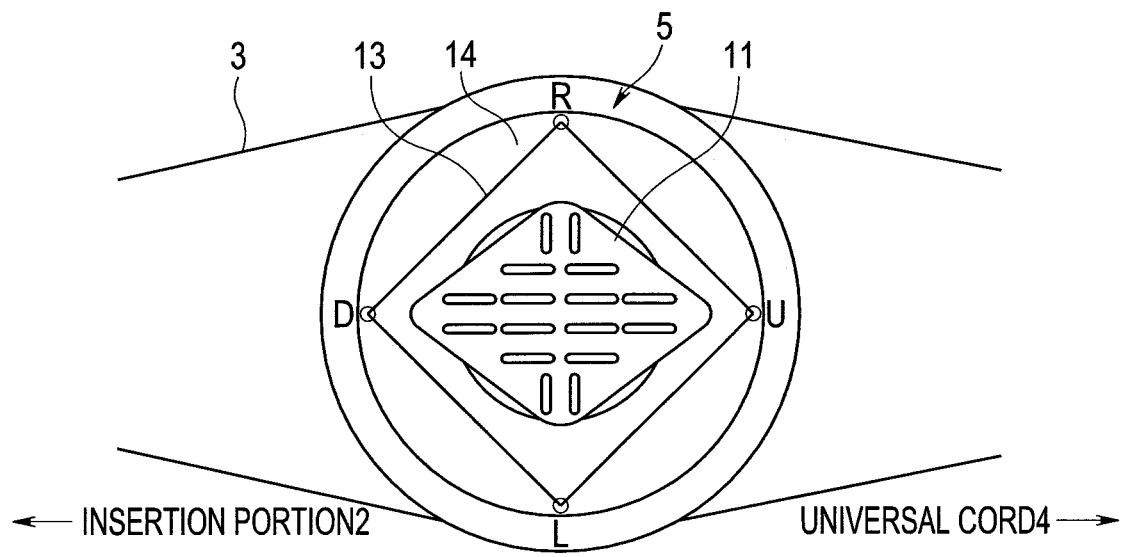
FIG. 6 is a plan view showing a configuration of a joystick lever mechanism provided on an operation portion according to a first modification.

As shown in FIG. 6, shape of the finger rest portion 11 may be made rhombic to conform to the outer circumferential shape of the rubber boot 13. Such a shape of the finger rest portion 11 makes it easier to recognize the directions in which the bending portion 7 is to be bent.

Second Modification

Figure 7:
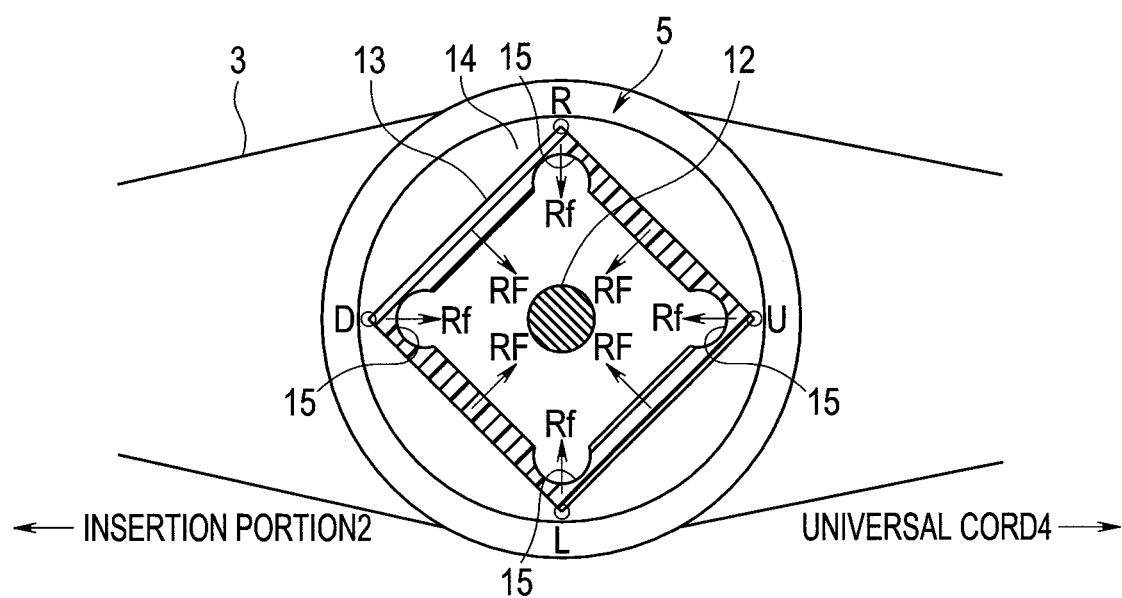
FIG. 7 is a partial cross-sectional view showing a configuration of a rubber boot according to a second modification.

As shown in FIG. 7, recessed portions 15 may be formed in the rubber boot 13 such that the four corners having the vertices U, D, R, and L are smaller in wall thickness than four side portions to reduce amounts of operating force needed to tilt the joystick lever mechanism 5 up, down, left, and right (UP, DOWN, LEFT, and RIGHT).

In other words, the rubber boot 13 is provided with deformability such that rigidity Rf of the four corners is lower than rigidity RE of the four side portions (Rf<RE), To put it another way, the rigidity of the rubber boot 13 is set to change in a circumferential direction of the rod 12, with deformable directions and less deformable directions being provided.

Consequently, by tilting the rod 12 through thumb-operation or the like on the finger rest portion 11 by following a sense of lightness or heaviness of amounts of operating force without visually checking operation directions of the joystick lever mechanism 5, the user can recognize the directions in which the joystick lever mechanism 5 is to be operated in order to bend the bending portion 7 in the up, down, left, and right (UP, DOWN, LEFT, and RIGHT) directions.

Besides, the rod 12 of the joystick lever mechanism 5 is returned to an initial position (neutral position) in center by the rigidity RE of the tour side portions.

Consequently, with the thumb or the like put lightly on, or taken off, the finger rest portion 11 of the joystick lever mechanism 5, the user can easily recognize that the rod 12 has returned to the neutral position and the bending portion 7 has become rectilinear. This makes it possible to cause the subject to directly face and squarely look at the distal end portion 6 of the endoscope 1.

Regarding the rubber boot 13, in setting the rigidity Rf of the four corners lower than the rigidity RF of the four side portions (Rf<RF), hardness, shape, material quality, or the like of the rubber may be used rather than wall thickness.

Third Modification

Figure 8:
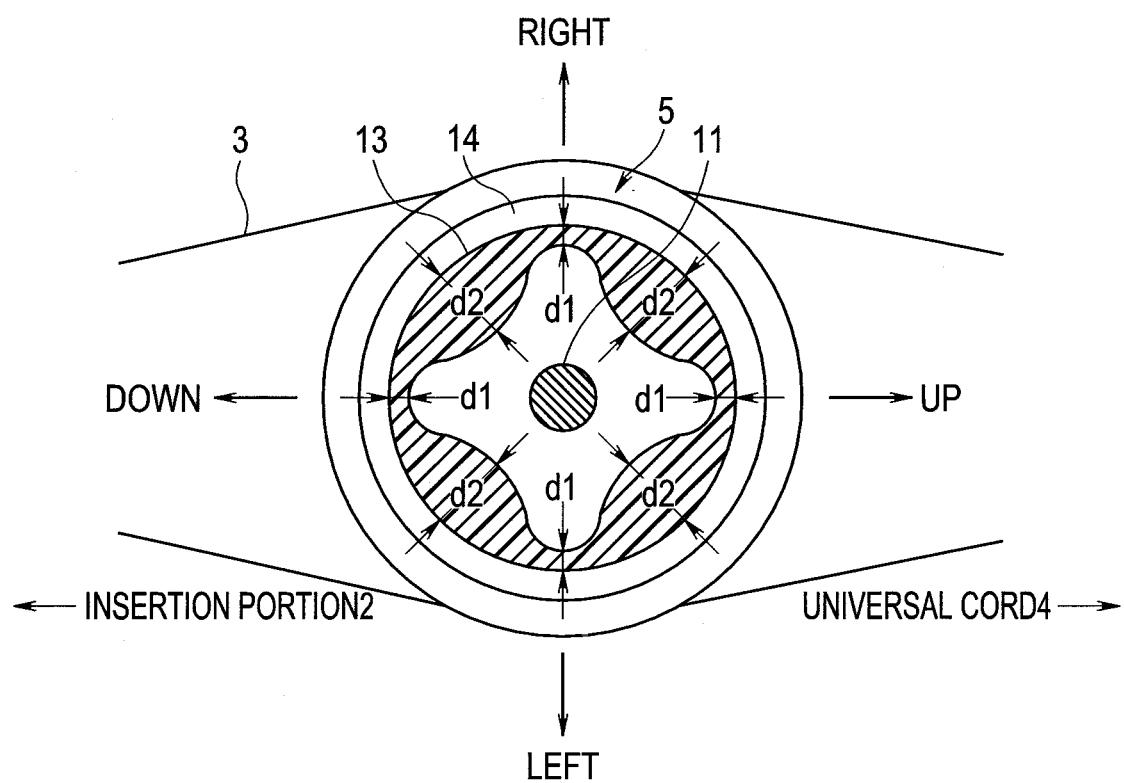
FIG. 8 is a partial cross-sectional view showing a configuration of a rubber boot according to a third modification.

As shown in FIG. 8, as with the second modification, the rubber boot 13 here may be made circular in outer circumference and sat to be deformable so as to reduce the amounts of operating force needed to tilt the joystick lever mechanism 5 up, down, left, and right (UP, DOWN, LEFT, and RIGHT) by making wall thickness d1 in directions corresponding to the U, D, R, and L directions smaller than wall thickness d2 in other directions.

With such a configuration, as with the second modification, the user can recognize the directions in which the joystick lever mechanism 5 is to be operated in order to bend the bending portion 7 in the up, down, left, and right (UP, DOWN, LEFT, and RIGHT) directions by following a sense of lightness or heaviness of amounts of operating force needed to tilt the rod 12 through thumb-operation or the like on the finger rest portion 11 without visually checking operation directions of the joystick lever mechanism 5.

Again, the rigidity in directions other than the directions corresponding to the U, D, R, and L directions is higher than the rigidity in the directions corresponding to the U, D, R, and L directions, which causes the rod 12 of the joystick lever mechanism 5 to return to the initial position (neutral position) in center, allowing the user to easily recognize that the bending portion 7 has become rectilinear.

Fourth Modification

Figure 9:
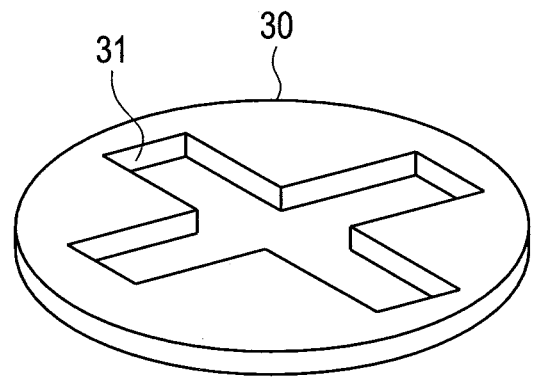
FIG. 9 is a perspective view showing a configuration of a guide seat according to a fourth modification.
Figure 10:
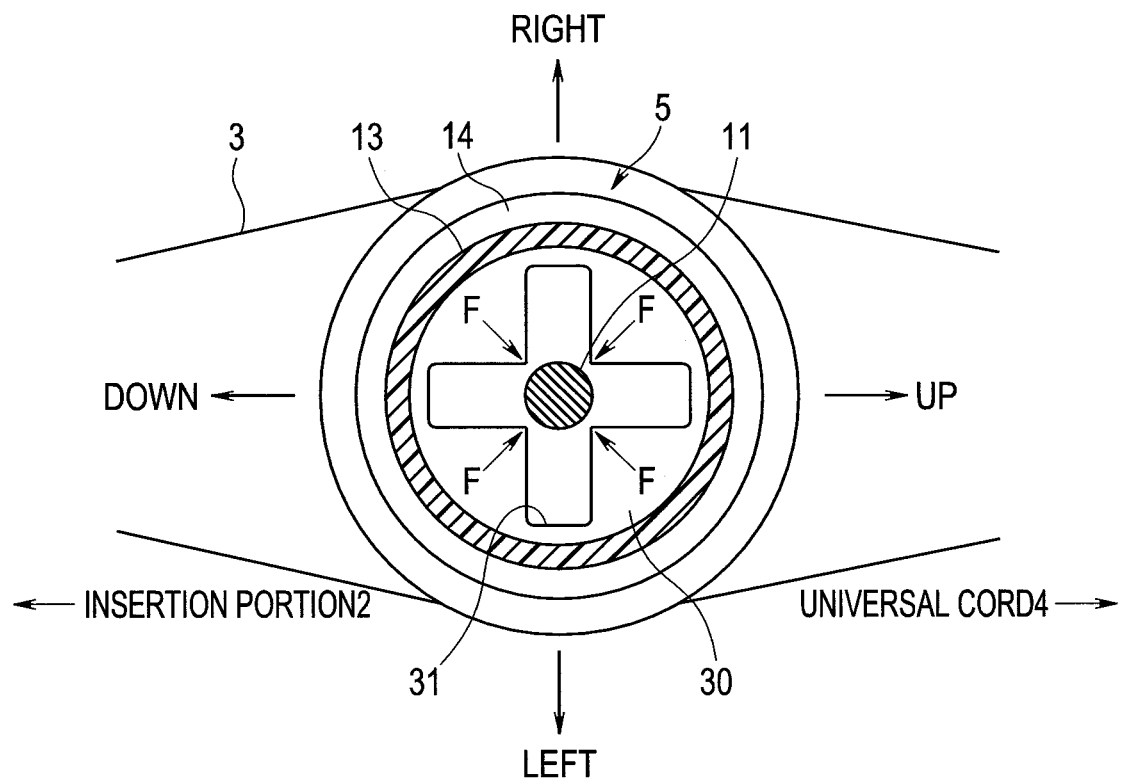
FIG. 10 is a partial cross-sectional view showing a joystick lever mechanism provided with the guide seat, according to the fourth modification.

As shown in FIGS. 9 and 10, the joystick lever mechanism 5 may be configured, for example, such that a guide seat 30, which is a disc-shaped elastic member made of rubber, is installed in the rubber boat 13, circular in outer circumference.

The guide seat 30 includes a holed portion 31 in which linear slits with a predetermined width are cut crosswise intersecting each other at right angles. The guide seat 30 is installed in the rubber boot 13 by aligning the directions of the orthogonally intersecting linear slits in the holed portion 31 with the operation directions of the joystick lever mechanism 5 used to bend the bending portion 7 up, down, left, and right (UP, DOWN, LEFT, and RIGHT).

With this configuration, in the operation directions used to bend the bending portion 7 up, down, left, and right (UP, DOWN, LEFT, and RIGHT), the rod 12 of the joystick lever mechanism 5 tilts along the holed portion 31 in the guide seat 30 without touching the guide seat 30.

On the other hand, when being tilted in such a direction as to bend the bending portion 7 obliquely, the rod 12 of the joystick lever mechanism 5 encounters resistance in F directions by contacting the guide seat 30 and thereby becomes difficult to tilt.

This automatically makes it easy for the user to tilt the joystick lever mechanism 5 in the operation directions used to bend the bending portion 7 up, down, left, and right (UP, DOWN, LEFT, and RIGHT), allowing the user to recognize the directions in which the joystick lever mechanism 5 is to be operated in order to bend the bending portion 7 in the up, down, left, and right (UP, DOWN, LEFT, and RIGHT) directions without visually checking the operation directions.

The invention described in the above embodiment and modifications are not limited to the embodiment and modifications, and may be modified in various forms in the implementation stage without departing from the gist of the invention. Furthermore, the embodiment and modifications described above include inventions at various stages, and various inventions can be extracted through appropriate combinations of the disclosed components.

For example, even if some of the components are removed from any of the embodiment and modifications, the resulting configuration can be extracted as an invention as long as the configuration can solve the problems described above and provide the advantages described above.

What is claimed is:

1. An insertion device comprising:
an insertion portion having a longitudinal axis;

a bending portion provided in the insertion portion and configured to be bendable from the longitudinal axis;
an operation portion provided proximally relative to the insertion portion;
an operation lever provided in the operation portion and having a shaft configured to cause the bending portion to bend when the operation lever is tilted; and
an elastic member comprising:
a first portion connected to the shaft,
a second portion connected to the operation portion,
a first rigidity that resists tilting of the operation lever in a first tilting direction, and
a second rigidity, greater than the first rigidity, that resists tilting of the operation lever in a second tilting direction,
wherein the elastic member having an inner cavity having a rectangular shape in a cross-section orthogonal to an axial direction of the shaft, and
a corner of the rectangular shape of the cross-section corresponds to the first tilting direction.

2. The insertion device according to claim 1, wherein the first tilting direction is a direction in which the operation lever causes the bending portion to bend in any of up, down, left, and right directions.

3. The insertion device according to claim 1, wherein a corner portion of the elastic member corresponding to the first tilting direction is formed to be smaller in wall thickness than a wall portion of the elastic member corresponding to the second tilting direction.

4. The insertion device according to claim 1, wherein a corner portion of the elastic member corresponding to the first tilting direction is formed to have lower hardness than a wall portion of the elastic member corresponding to the second tilting direction.

5. The insertion device according to claim 1, wherein the operation lever is a joystick lever made up of the shaft on which a finger rest portion is provided, and the elastic member is a rubber boot.

6. The insertion device according to claim 1, wherein the insertion device is an endoscope.

7. The insertion device according to claim 1, wherein the elastic member further having an outer periphery having a rectangular shape in the cross-section orthogonal to the axial direction of the shaft.

8. The insertion device according to claim 7, wherein
the elastic member having four corners on the outer periphery; and
the shaft having a finger rest disposed on a free end of the shaft, the finger rest portion having four corners positioned to align with the four corners of the elastic member.

9. The insertion device according to claim 7, wherein
the bending portion is configured to be bendable from the longitudinal axis in up, down, left, and right directions;
the elastic member having four corners on the outer periphery corresponding to the up, down, left, and right directions, respectively.

10. The insertion device according to claim 1, wherein the rectangular shape of the inner cavity having rounded corners.

11. An operation portion for use with an insertion device, the operation portion comprising:
an operation portion body;
an operation lever projecting from the operation portion body and having a shaft configured to cause a bending portion of an insertion portion having a longitudinal axis to bend from the longitudinal axis when the operation lever is tilted; and;
an elastic member comprising:
a first portion connected to the shaft,
a second portion connected to the operation portion body,
a first rigidity that resists tilting of the operation lever in a first tilting direction, and
a second rigidity, greater than the first rigidity, that resists tilting of the operation lever in a second tilting direction,
wherein the elastic member having an inner cavity having a rectangular shape in a cross-section orthogonal to an axial direction of the shaft, and
a corner of the rectangular shape of the cross-section corresponds to the first tilting direction.

12. The operation portion of the insertion device according to claim 11, wherein the first tilting direction is a direction in which the operation lever causes the bending portion to bend in any of up, down, left, and right directions.

13. The operation portion of the insertion device according to claim 11, wherein a corner portion of the elastic member corresponding to the first tilting direction is formed to be smaller in wall thickness than a wall portion of the elastic member corresponding to the second tilting direction.

14. The operation portion of the insertion device according to claim 11, wherein a corner portion of the elastic member corresponding to the first tilting direction is formed to have lower hardness than a wall portion of the elastic member corresponding to the second tilting direction.

15. The operation portion of the insertion device according to claim 11, wherein the operation lever is a joystick lever made up of the shaft on which a finger rest portion is provided, and the elastic member is a rubber boot.

16. The operation portion according to claim 11, wherein the elastic member further having an outer periphery having a rectangular shape in the cross-section orthogonal to the axial direction of the shaft.

17. The operation portion according to claim 16, wherein
the elastic member having four corners on the outer periphery; and
the shaft having a finger rest disposed on a free end of the shaft, the finger rest portion having four corners positioned to align with the four corners of the elastic member.

18. The insertion device according to claim 16, wherein
the bending portion is configured to be bendable from the longitudinal axis in up, down, left, and right directions;
the elastic member having four corners on the outer periphery corresponding to the up, down, left, and right directions, respectively.

19. The operation portion according to claim 11, wherein the rectangular shape of the inner cavity having rounded corners.

20. An insertion device comprising:
an insertion portion having a longitudinal axis;
a bending portion provided in the insertion portion and configured to be bendable from the longitudinal axis;
an operation portion provided proximally relative to the insertion portion;
an operation lever provided in the operation portion and having a shaft configured to cause the bending portion to bend when the operation lever is tilted; and
an elastic boot comprising:
a first portion connected to the shaft,
a second portion connected to the operation portion, a first rigidity that resists tilting of the operation lever in a first tilting direction, and a second rigidity, greater than the first rigidity, that resists tilting of the operation lever in a second tilting direction, wherein the elastic boot having an outer rectangular shape in a cross-section orthogonal to an axial direction of the shaft, and a corner of the rectangular shape of the cross-section corresponds to the first tilting direction.

* * * * *